(12) United States Patent
Neuberger

(10) Patent No.: US 7,976,571 B2
(45) Date of Patent: Jul. 12, 2011

(54) PHOTODYNAMIC THERAPY IRRADIATION SYSTEM FOR THE TREATMENT OF SUPERFICIAL HYPERPROLIFERATIVE TISSUE GROWTH

(76) Inventor: Wolfgang Neuberger, Labuan (MY)

( * ) Notice: Subject to any disclaimer, the term of this patent is extended or adjusted under 35 U.S.C. 154(b) by 855 days.

(21) Appl. No.: 11/195,106

(22) Filed: Aug. 2, 2005

(65) Prior Publication Data

US 2007/0032845 A1    Feb. 8, 2007

(51) Int. Cl.
*A61N 5/067*    (2006.01)
(52) U.S. Cl. ............................................. 607/89; 607/88
(58) Field of Classification Search ................ 606/8–15; 607/88–104; 128/898
See application file for complete search history.

(56) References Cited

U.S. PATENT DOCUMENTS

| | | | | |
|---|---|---|---|---|
| 5,000,752 A * | 3/1991 | Hoskin et al. | | 606/9 |
| 5,616,140 A * | 4/1997 | Prescott | | 606/10 |
| 6,152,918 A * | 11/2000 | Padilla et al. | | 606/15 |
| 6,355,054 B1 * | 3/2002 | Neuberger | | 607/89 |
| 6,416,531 B2 * | 7/2002 | Chen | | 607/89 |
| 7,125,416 B2 * | 10/2006 | Kent et al. | | 607/88 |
| 7,422,598 B2 * | 9/2008 | Altshuler et al. | | 607/93 |
| 2004/0215292 A1 | 10/2004 | Chen | | |
| 2004/0260367 A1 * | 12/2004 | De Taboada et al. | | 607/88 |
| 2004/0267335 A1 * | 12/2004 | Tulip et al. | | 607/89 |
| 2006/0095095 A1 * | 5/2006 | Cao | | 607/88 |
| 2008/0249517 A1 * | 10/2008 | Svanberg | | 606/15 |

* cited by examiner

*Primary Examiner* — Ahmed M Farah
(74) *Attorney, Agent, or Firm* — Bolesh J. Skutnik; BJ Associates

(57) ABSTRACT

A device and method is described for photodynamic therapy (PDT) to treat hyperproliferative tissue growth in an underskin area within a few centimeters of the skin surface that is not accessible by conventional topical irradiation. The device comprises a plate having an array of openings with hollow micro-needles mounted therein that extend to a specified length on each side. Optical fibers are individually threaded through the micro-needles from the side opposite the treatment area and may be kept together as a bundle for attachment to a laser radiation source. The optical fibers have output ends made to provide a uniform radiation pattern to the underlying tissue. A photosensitizer is administered either systemically or locally and allowed a sufficient time to diffuse into the area of treatment. The laser of selected wavelength is coupled to the fiber bundle which then directs the radiation through the optical fibers to the treatment site.

16 Claims, 5 Drawing Sheets

PHOTODYNAMIC THERAPY IRRADIATION SYSTEM FOR THE TREATMENT OF SUPERFICIAL HYPERPROLIFERATIVE TISSUE GROWTH

BACKGROUND OF THE INVENTION

1. Field of the Invention

The present invention relates to a device and method for photodynamic therapy (PDT) that is capable of treating hyperproliferative tissue growth existing deeper in the body than is accessible to successful treatment by direct topical irradiation, while minimizing unnecessary surface skin damage.

2. Invention Disclosure Statement

There are various ways to treat hyperproliferative tissue growth in the body. Traditional approaches involve surgery, chemotherapy, and x-ray radiation to reduce or eliminate the tissue growth. A relatively new approach, photodynamic therapy (PDT), involves the use of photosensitizers and laser radiation provided through optical fibers to areas of tissue growth. PDT is a three step treatment process: in the first step, a photosensitive compound is administered systemically by injection or topically to a treatment site on the patient's body; and after a sufficient time to allow the photosensitizer to be absorbed, the treatment site is irradiated with a light having a wavelength corresponding to the characteristic absorption wavelength of the photosensitizer. The light activates the photosensitizer causing singlet oxygen radicals to be generated leading to biological effects that destroy the hyperproliferative tissue. The depth of penetration of the cytotoxic effect in the tissue depends on the depth of light penetration, the concentration and cellular distribution of photosensitizer in the tissue and the availability of molecular oxygen in the abnormal tissue or tumor.

PDT laser source wavelengths are selected based on the photosensitizer. It is seen that large tumors or tumors that are embedded beneath skin layers are difficult to reach and destroy completely because of the skin. Various devices and methods have been proposed to overcome this issue of deep lying tumors. Devices have been proposed that can treat these tissues to a limited depth and effectiveness of destruction. With a conventional external light source cytotoxicity in tissue during PDT is limited to a depth of about 5 mm, minimally for depth ranges from 5 mm to 10 mm and almost negligible for greater than 10 mm.

The outermost stratum corneum layer of the epidermis layer of the skin presents the most resistance to light irradiation. There is substantially less resistance to penetration in the subsequent epidermal and dermal layers of the skin. In order to target a large tumor or tumor residing deep in the skin layers, a means to deliver radiation to the target tissue is necessary for effective treatment.

Treatment of tumors by the use of an external light irradiation can lead to damage of healthy skin not only from the light but from the activation of the photosensitizer in that area. Photosensitizer accumulation is required to treat tumor tissue growth but with the availability of atmospheric oxygen in healthy skin layers followed by light activation or radiation can lead to unwanted skin damage. Various solutions have been proposed to eliminate these complications. In most topical radiation treatments, these upper layers of skin are damaged even when precautions are taken. Some methods use a cooling mechanism to minimize effects to the skin prior, during and after treatment.

U.S. Pat. No. 5,000,752 by Hoskin et al., entitled, "Treatment Apparatus and Method," describes a method for transdermal laser delivery by the insertion of an array of needles fixed on a flexible plate into a port wine stain treatment site. Spear-like tips that aid in the breaking of the skin surface and diffusing of the radiation are attached to the needles; optical fibers are attached to the tips within the needles. The tips have a diameter equal to the diameter of the needles and may cause unnecessary surface skin damage. The needles have specialized and adjustable tips which makes the device expensive and difficult to sterilize. Since the tip of the needle must be in the area of treatment, a larger diameter hole is created into the skin. Further, adjustment of the depth of the needle is not disclosed and therefore treatment of hyperproliferative tissue beyond the port wine stain deep is not achieved as in the present invention with minimum of damage to the tissue.

In Publication US 2004/0215292 by Chen, a method is defined for transcutaneously administering photodynamic therapy to a target tissue that lies deep below the skin. The method involves the introduction of a photosensitizing agent or a photosensitizing agent delivery system or a prodrug product that selectively binds to the target tissue. A low intensity light with a waveband corresponding to the absorption wavelength of the photosensitizer is applied for a long duration of time. After the drug binds to the target tissue and upon initiation of light activation in the surrounding tissue there results blood vessel closure/thrombosis in the surroundings. This is followed by targeting the treatment site with irradiation to ensure damage of the tumor. This is a very lengthy process of irradiating target tissue with a low fluence of radiation for about 3 to 24 hours to reduce skin or surrounding tissue damage.

An ideal device for the present invention would be one able to protect the stratum corneum (~20 μm), the epidermis (~100 μm) and the dermal (~1200 μm) layers, and deliver radiation beyond the hypodermal (~1200 μm) layer of skin where the healthy surface skin layers are minimally irradiated. The device would be one which will deliver light irradiation to the deep lying tumor in order to provide uniform tissue destruction at the treatment site. Hence a device and method is needed to target the deep and large hyperproliferative tissue with improved laser delivery without the complications associated with the prior art.

OBJECTIVES AND BRIEF SUMMARY OF THE INVENTION

It is an object of the present invention to provide a device and method for photodynamic therapy (PDT) that is capable of treating tumors or other hyperproliferative tissue growth existing near the skin surface and deeper in the body than is accessible by standard topical irradiation and without the complications associated with the prior art.

It is another object of the present invention to insert a means to deliver the irradiation into the treatment site to enhance safe radiation delivery through the epidermis and dermis.

It is still another object of the present invention to provide a means to deliver the irradiation through a plate which consists of micro-needles with optical fibers therein to deliver radiation to an underskin treatment site.

It is further object of the present invention to treat deep lying or extensive tumors that are not accessible by topical radiation.

It is still further object of the present invention to treat deeper tumors with minimal damage to skin layers which are healthy.

It is yet another aim of the present invention to provide a micro-needle with an optical fiber therein having a diffuser tip at its treatment end to enhance radiation delivery in the tissue.

Briefly stated, a device and method is described for photodynamic therapy (PDT) to treat hyperproliferative tissue growth in an underskin area within a few centimeters of the skin surface that is not accessible by conventional topical irradiation. The device comprises a plate having an array of openings with hollow micro-needles mounted therein that extend to a specified length on each side. Optical fibers are individually threaded through the micro-needles from the side opposite the treatment area and may be kept together as a bundle for attachment to a laser radiation source. The optical fibers have output ends made to provide a uniform radiation pattern to the underlying tissue. A photosensitizer is administered either systemically or locally and allowed a sufficient time to diffuse into the area of treatment. The laser of selected wavelength is coupled to the fiber bundle which then directs the radiation through the optical fibers to the treatment site.

The above and other objects, features and advantages of the present invention will become apparent from the following detailed description read in conjunction with the accompanying drawings.

DETAILED DESCRIPTION OF PREFERRED EMBODIMENTS

Figure 1:
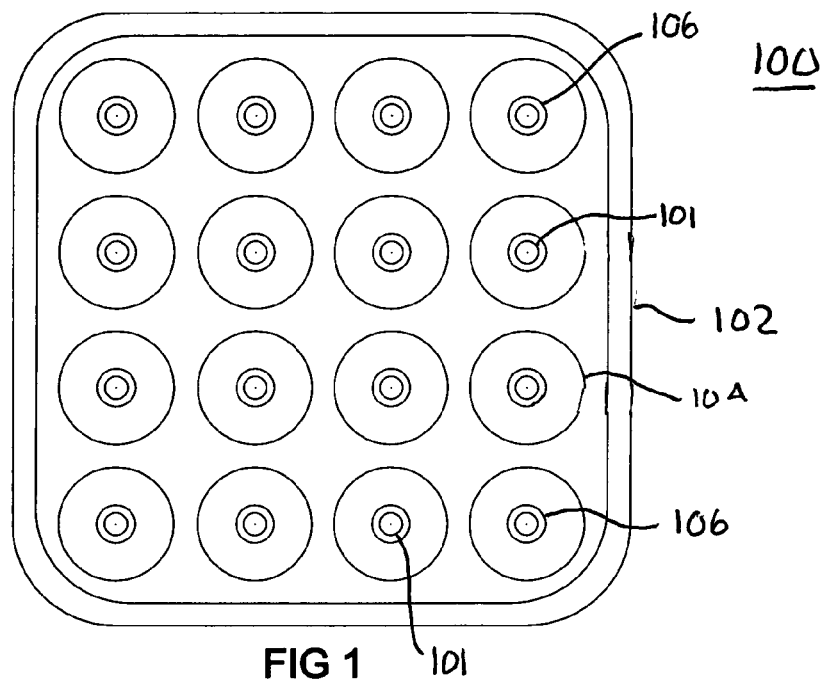
FIG. 1 illustrates a micro-needle array upon a plate for placement upon the skin of a patient.

The present invention describes a device and a method of providing PDT to treat hyperproliferative tissue growth which normally cannot be adequately treated from outside of the patient's skin since the objective of the treatment is to produce cytotoxicity in deep and/or large hyperproliferative tissue growth to ensure complete and uniform destruction of the tissue lying below the skin.

To achieve this result a micro-needle plate is first placed on the treatment site over the diseased tissue growth area. The plate may be pliable to a degree so as to conform to body curves such as exist on the neck, face, arms and legs. This plate is designed to hold micro-needles that extend from the plate on both sides. The micro-needles may be permanently mounted in the plate or be adjustable. A bandage may hold the plate to the body area but other devices may be used such as extendable straps and this should not be considered a limiting feature of the invention. On the treatment side of the plate, the micro-needles may have an appropriate diameter to puncture the skin such as a 50 μm diameter micro-needle. The micro-needles may be pointed or blunt shaped and positioned to extend to a depth of from about 2 to 10 mm depending on the depth of tissue to be treated. The micro-needles may be uniformly located in the plate and are set on the plate at distances of 3 to 5 mm on center from each other. These needles have the capability to deliver and channel laser radiation deep into the tissue below the skin. After the plate is positioned on the skin, optical fibers are fed into the micro-needles a predetermined distance. The optical fibers have output ends that are shaped to deliver laser radiation uniformly as well as ease the insertion of the optical fiber through the tissue. The output ends may extend from the micro-needle. Since the micro-needles penetrate the upper layers of skin to target the deep lying tissue, the openings created in the skin by the micro-needles are comparable to the size of other openings in the skin tissue; hence they pose a minimum risk of infection or permanent damage to the layers of skin or pain to the patient.

The present invention allows for the delivery of laser radiation to a treatment site. The advantage of this device and method is the use of micro-needles to deliver the laser radiation to the deep lying tissue. The micro-needles are minimally invasive and the micro-pores formed are very small to prevent any infection in the skin layers as well as to expedite healing.

The device employs a micro-needle plate with optical fibers threaded into the micro-needles to deliver the laser radiation to the target sites. The needles may have the capability to be advanced in either direction of the plate. The optical fibers are individually threaded into the micro-needles at the proximal end of micro-needle. The reason for advancing the proximal side of micro-needle is to hold the optical fiber securely and align the output end from the fiber into micro-needle. The input portions of the fibers are combined to form a bundle which is connected to the laser source at the proximal end of fibers.

FIG. 1 illustrates a micro-needle plate 100 with micro-needles 106 arranged in a symmetric array. Micro-needles 106 are positioned at distances of about 3 to 6 mm on center from the closest adjacent micro-needle. The pattern illustrated is a preferred pattern but is not necessarily the only possible pattern allowed. Further, the number of micro-needles 106 in the array shown may increase as the square of integers. Whether there are optical fibers 101 placed in needles 106 is determined by the area of treatment; therefore it is not necessary that all micro-needles 106 in the array have optical fibers 101 therein. The plate 100 may have means to hold the micro-needles 106 in the target tissue through securing bandage 102 about the plate 100. Elastic straps or bandages may be used as determined by the body part. After the micro-needles are inserted, pliable plate 100 may be retained on the treatment site due to friction only. Micro-needles 106 are held in place by holding mechanism 104 present on both sides of plate 100 to be detailed below. Holding mechanism 104 is necessary to precisely determine the amount of depth the needles penetrate into the skin based on the distance and size of tumor.

Figure 2:
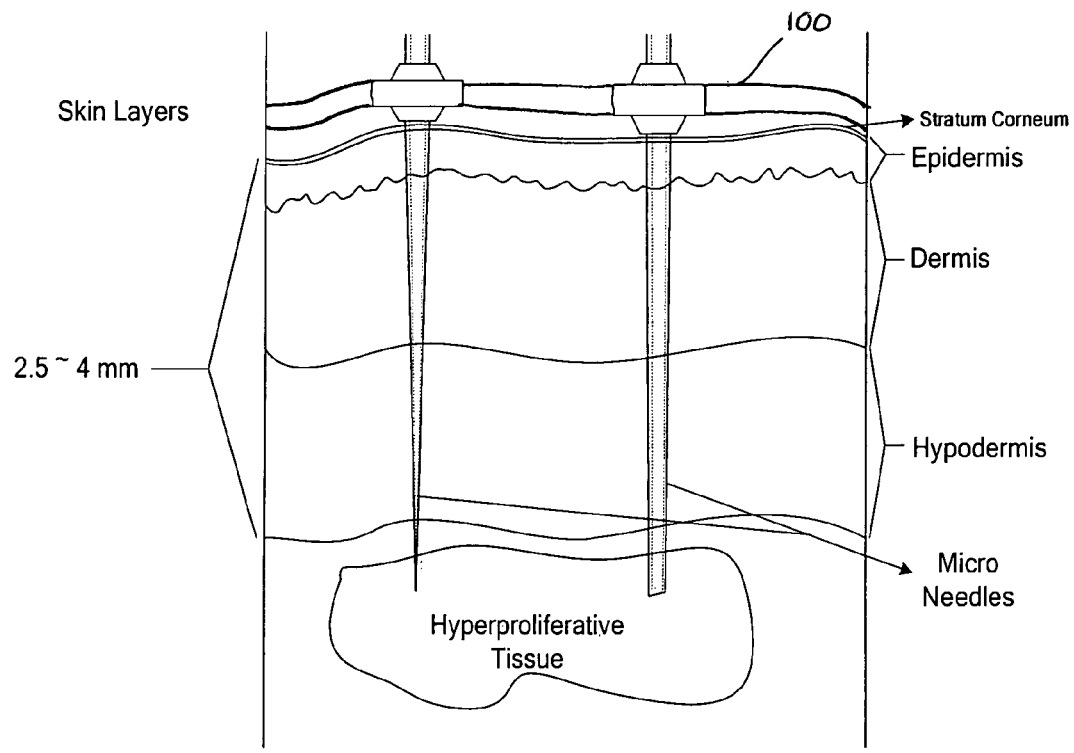
FIG. 2 schematically illustrates the placement of the micro-needles on the plate in skin layers.

FIG. 2 is a schematic illustration of the skin layers relative to the size and depth to which the micro-needles penetrate to target the hyperproliferative tissue. FIG. 2 shows the layers of skin consisting of epidermal, dermal and hypodermal layers. Micro-needles 106 are capable of penetrating to varied depths ranging from 0 to 10 mm, for example. The thickness of the plate 100 is not in proportion to the skin layers shown.

Figure 3A:
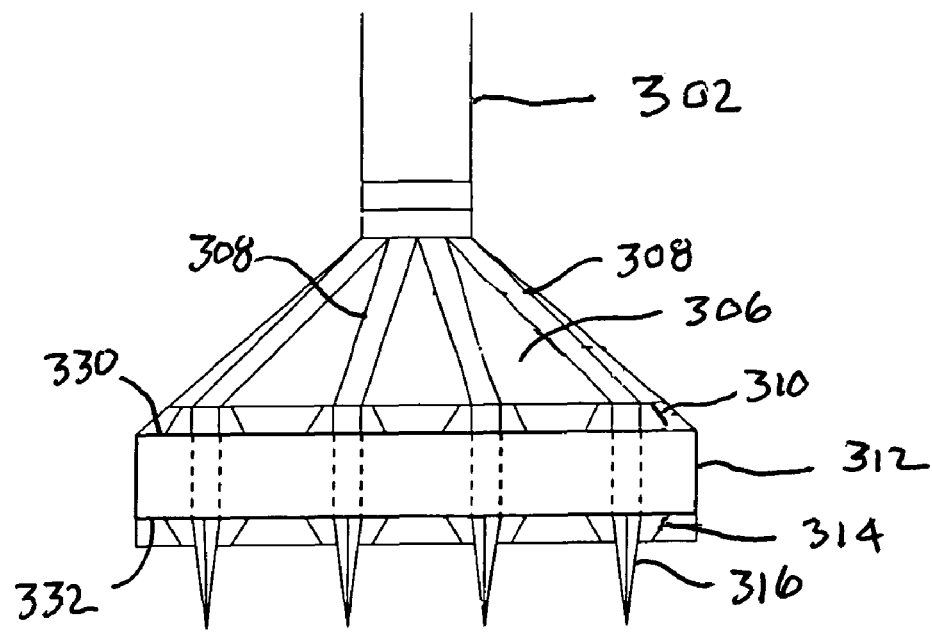
FIG. 3A illustrates a bundled optical fiber with delivery means to connect the fiber means to the micro-needle plate which has pointed needles to target deeper tissue.

FIG. 3A illustrates micro-needle plate 312 connected to optical fiber bundle 302. Fiber bundle 302 has individual fibers 308 enclosed in connection mechanism 306. Connection mechanism 306 may be represented by the proximal ends of the micro-needles 316 extending from plate 312. Advancement means 310 on a back side 330 of plate 312 and advancement means 314 on a treatment side 332 of plate 312 are used to adjust the distance of micro-needles 316 extending from the treatment side 332. Although not shown, micro-needles 316 may be welded, glued, or otherwise fixedly attached to the plate 100, and therefore there may be a set of plates having appropriate number of micro-needles thereon with predetermined micro-needles extensions. This would minimize any time needed in this procedure in regards to selecting plates. Further, the number and placement of the optical fibers in the micro-needles is a variable determined by the patient and the area of treatment. Micro-needle 316 is pointed to enable deeper penetration into the target tissue and the output end of optical fiber 308 is appropriately designed to fit within micro-needle 316.

Figure 3B:
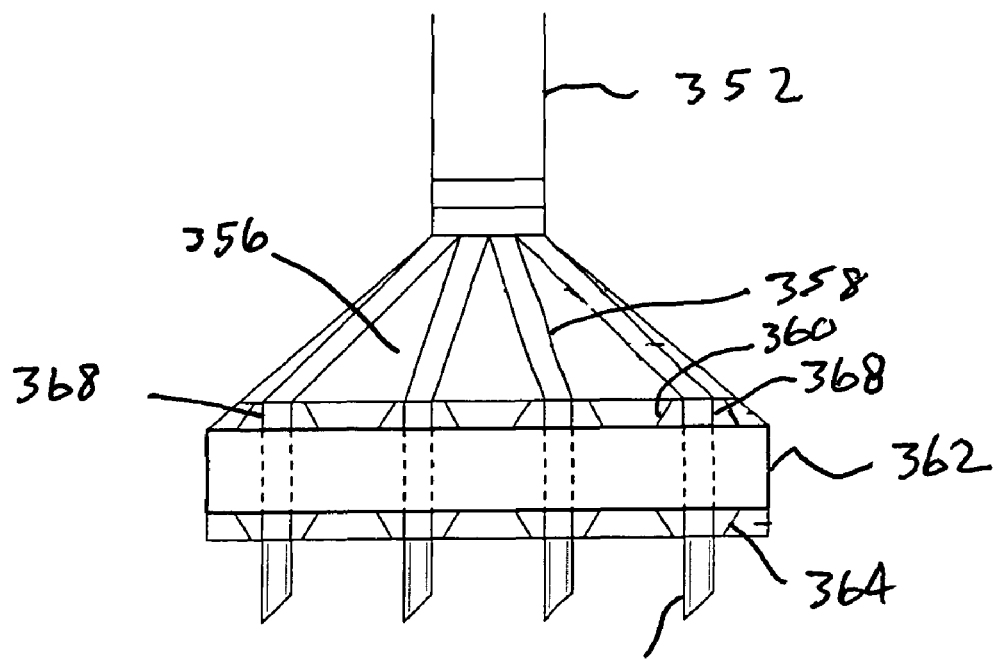
FIG. 3B illustrates a bundled optical fiber with delivery means to connect the fiber means to the micro-needle plate which has large diameter needles to target a larger area of tissues.

FIG. 3B illustrates micro-needle plate 362 connected to optical fiber bundle 352. Fiber bundle 352 is split at connector means 354 to individual fibers 358 enclosed in connection mechanism 356. Connection mechanism 356 links individual fibers 358 with micro-needles input ends 368. Advancement means 360 and 364 are similar to FIG. 3A. An output end 370 is shown as a larger diameter needle than in FIG. 3A.

Figure 4:
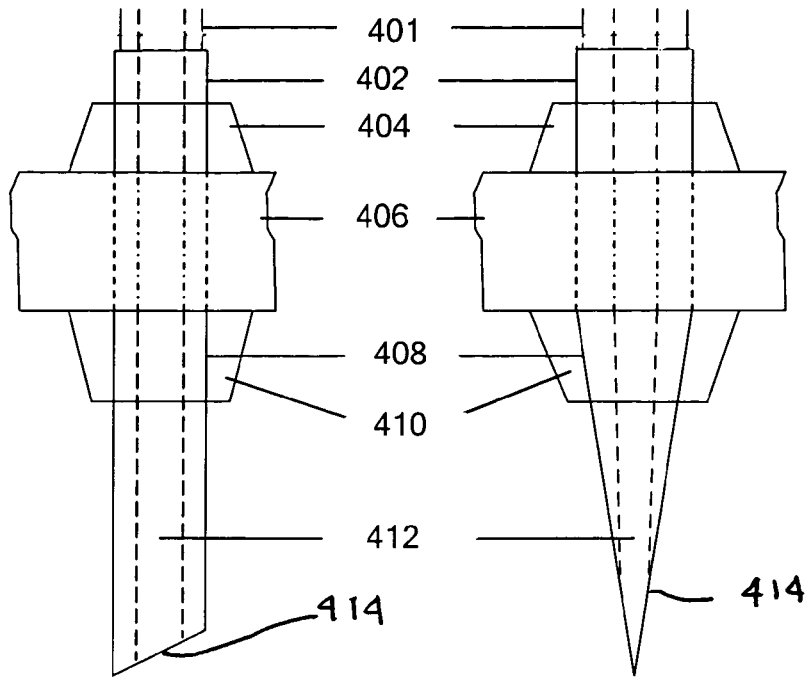
FIG. 4 illustrates a micro-needle with means to advance the micro-needle by a selected distance on either side of the plate and a pointed micro-needle showing the same.
Figure 5:
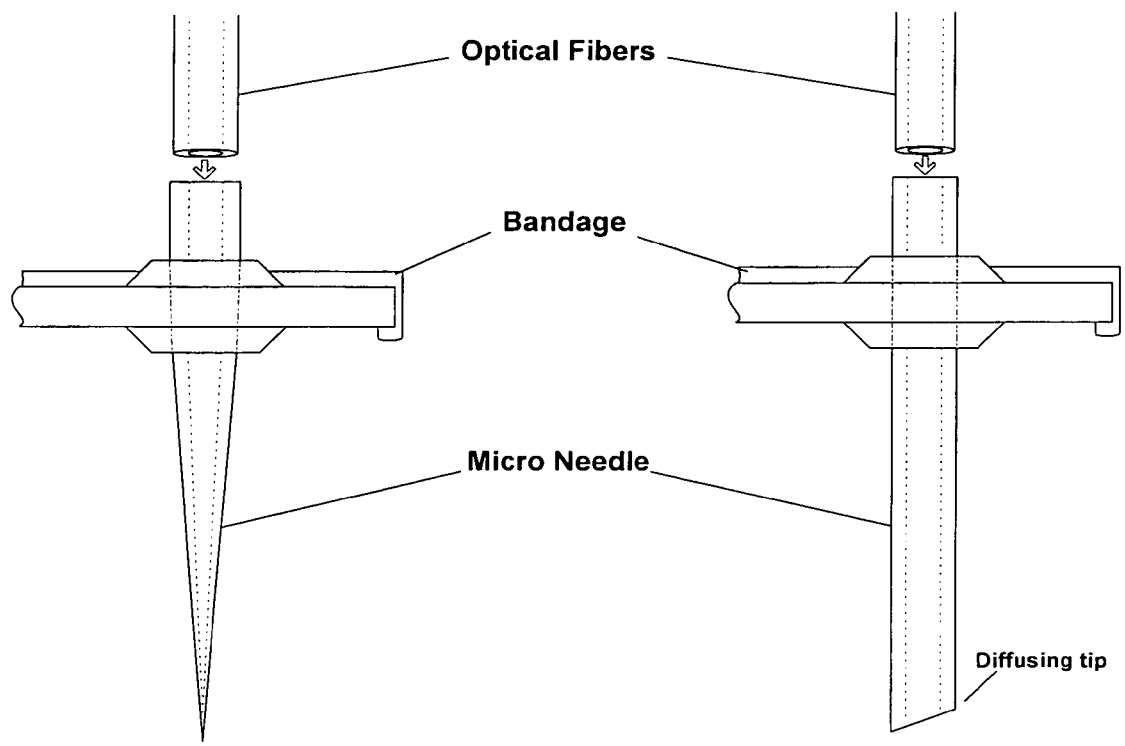
FIG. 5 illustrates a pointed micro-needle with an optical fiber and holding bandage and another micro-needle.

FIG. 4 shows a side view of the micro-needles in both the embodiments described in FIG. 3. Micro-needles 402 are inserted through plate 406 and optical fibers 401 are inserted into and through micro-needles 402. Advancement mechanism 404 on the top of the plate holds the proximal side of micro-needle 402 which is advanced to couple optical fiber 401 to needle core. Other advancement means 410 helps to advance the distal or treatment side micro-needle 408 to a desired depth anywhere from about 3 to 10 mm. This advancement means 410 also holds micro-needle 408 in place when it is inserted into a treatment site. The micro-needle has a central core 412 being a hollow channel through which the laser radiation passes to the treatment site. Output ends 414 of optical fibers 401 are appropriately designed and shaped to aid in the insertion of the optical fiber through tissue and outputting of laser radiation in a uniform manner. Initially, the optical fiber may not extend from the output end of the micro-needle FIG. 5 shows a cross sectional view of the plate with the bandage that anchors the plate. The lengths or thicknesses shown are not representative of actual sizes and merely to show general locations and positions of the objects relative to one another. The optical fibers are inserted into the proximal ends of the micro-needles where the fiber output end is effectively coupled into the tissue area of treatment. Initially the output end of the optical fiber is held within the needle and after insertion of the micro-needle into the skin, the optical fiber is advanced through the needle to reach the area of treatment. The distal or treatment side of micro-needle extends to varied depths based on tissue depth. Further, the micro-needles may be permanently mounted in the plate and would be non-adjustable. Whether the micro-needles are adjustable in the plate or permanently fixed therein are optional features. For example, a set of plates could be provided with micro-needles having different extensions for each plate and depending on the area of treatment, a particular plate would be selected. The bandage has a dual function of providing fixation and also giveing protection against stray radiation.

Figure 6:
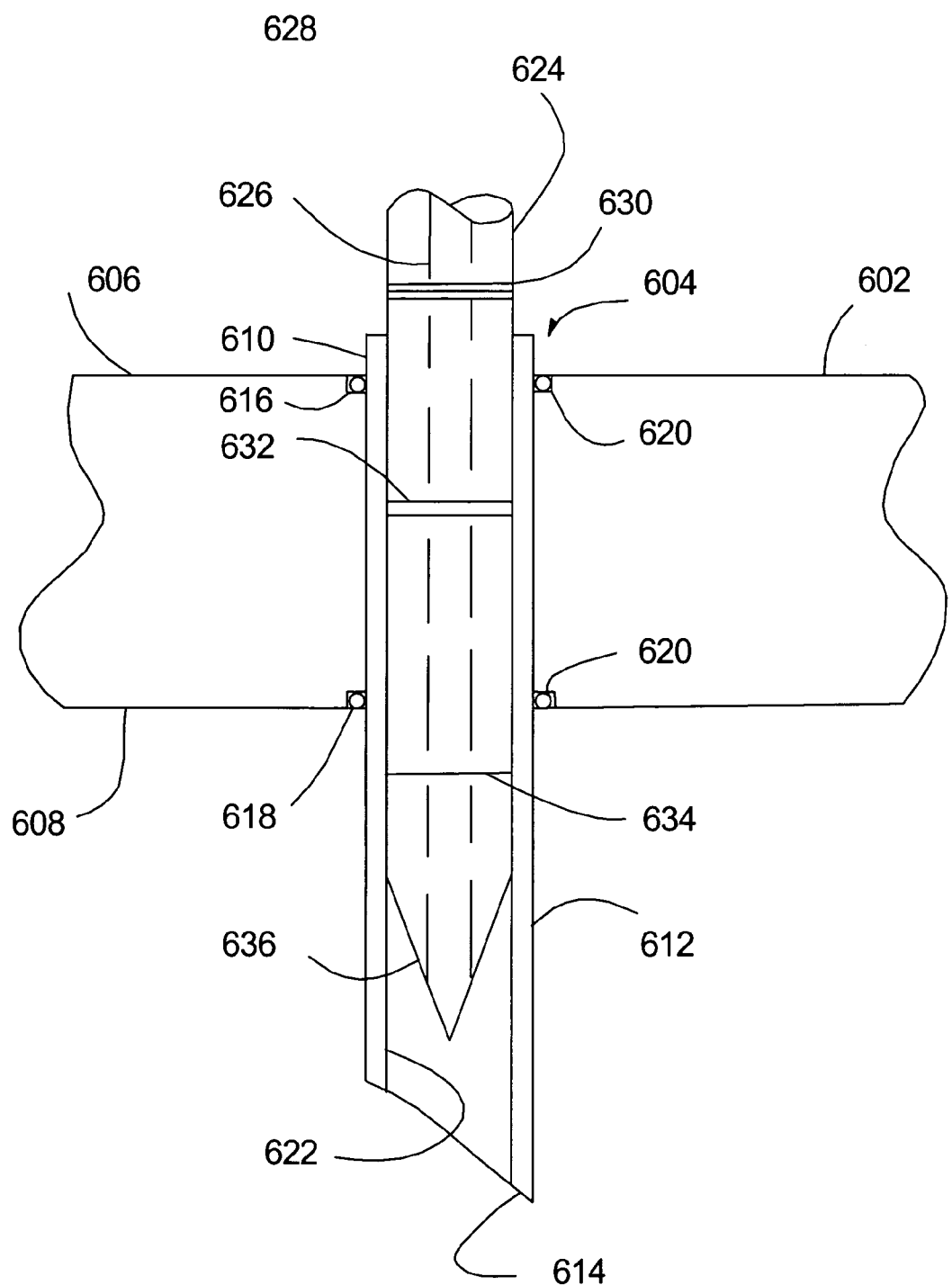
FIG. 6 illustrates by partial view a plate with a micro-needle with an optical fiber therein of the present invention.

FIG. 6 illustrates another embodiment of the present invention. Micro-needle plate 602 is only partially shown. Plate 602 may be a hard plastic or metal material. Plate 602 may be flexible or pliable to conform to the area of treatment. Plate 602 may be preformed in shape depending on the need and demand. Further, plate 602 may be made of a thermo-setting material which upon heating can be formed to the body shape of the area of treatment. A pad of material would be placed under plate 602 to prevent the micro-needles from penetrating the skin while shaping of the plate. Through plate 602 is an array of openings 604, only one shown, connecting a back side 606 and a treatment side 608. Into one or more openings 604 are inserted micro-needles 610 that extend from back side 606 and treatment side 608 predetermined distances, the treatment side distance being the distance that treatment end 612 extends into and through the skin, not shown. This distance is determined in advance by the location and dimensions of the tissue growth to be treated. Insertion end 614 of treatment end 612 of micro-needle 610 may be shaped as a point or as a blunt sharpened end such as shown. A back side adjustment o-ring 616 and a treatment side o-ring 618 are closely fitted into channels 620 to securely hold micro-needle 610 therein. With a sufficient force, micro-needle 610 may be adjusted in position within opening 604. Once micro-needle 610 is positioned in the opening, the force of inserting the micro-needle through the skin should not move the positioned micro-needle 610. Micro-needle 610 has an inside bore 622 that closely fits about an optical fiber 624 to be inserted therein. Each optical fiber 624 is connected to a laser source, not shown.

In order to determine the distance of insertion of optical fiber 624 into micro-needle 610, a plurality of external markings may be placed on the fiber's outer surface. As seen in FIG. 6, three distinctive bands 630, 632 and 634 are appropriately located along the length of the output end of optical fiber 624. For example, each band may be indicative of a depth of 2 millimeters. Other markings are clearly feasible. An output end 636 of optical fiber 624 is appropriately sharpened and shaped to provide ease of passage through the tissue and for providing uniform radiation to the treated tissue. Output end 636 may be advanced beyond insertion end 614 of micro-needle 610. Further, insertion end 614 provides lateral support to the output end of the optical fiber 624. The distance that insertion end 614 of micro-needle 610 extends beyond treatment side 608 and distance that output end 636 of optical fiber 624 extends beyond insertion end 614 is determined in advance based on the configuration of the tissue growth to be treated.

Figure 7:
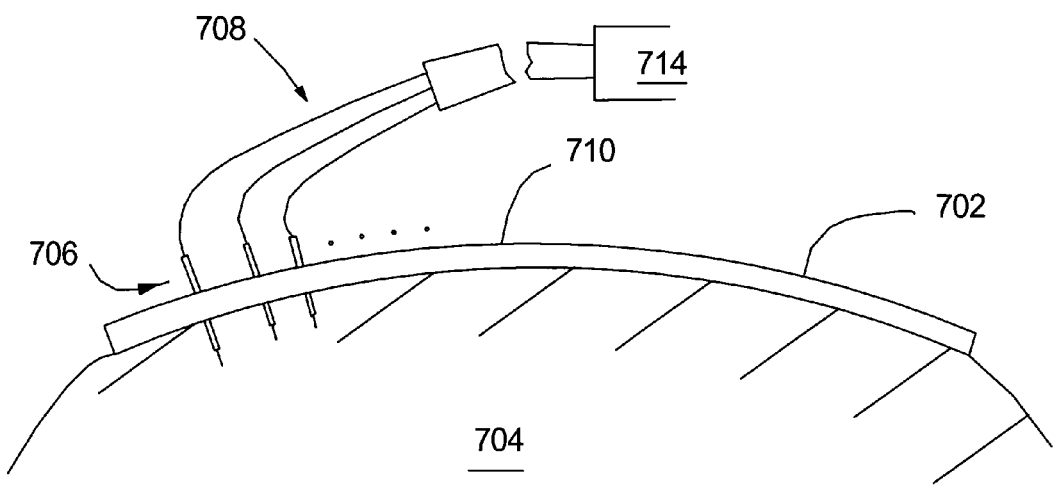
FIG. 7 illustrates a pliable plate having only a few of the micro-needles with optical fibers therein attached to a rounded body part.

FIG. 7 illustrates a pliable plate 702 mounted on a rounded body part 704 such as an arm or neck Plate 702 has a plurality of micro-needles 706 mounted therein which may be adjustable or fixedly attached thereto. Optical fibers 708 are attached to the micro-needles 706 on rear-side 710 of plate 702. The optical fibers 708 are formed into a bundle 712 which is attached to a laser source 714. Depending on the area of treatment, few than all of the micro-needles 706 and optical fibers 708 may be used.

Having described preferred embodiments of the invention with reference to the accompanying drawings, it is to be understood that the invention is not limited to the precise embodiments, and that various changes and modifications may be effected therein by one skilled in the art without departing from the scope or spirit of the invention as defined in the appended claims.

What is claimed is:

1. A photo dynamic therapy laser delivery system for the safe delivery of laser radiation to an area of treatment below a layer of skin comprising:
   a plate with a plurality of spaced openings, said plate having a treatment side and an insertion side, said spaced openings connecting said sides;
   micro-needles placed in the said spaced openings;
   first means for holding said micro-needles in said spaced openings in said plate; wherein said micro-needles extend beyond said treatment side, by a predetermined distance sufficient to penetrate through the skin;
   second means for holding said plate on said layer of skin;
   optical fibers placed in at least two of said micro-needles;
   third means for positioning said optical fibers in said micro-needles;
   wherein said optical fibers have proximal ends and distal ends, said proximal ends being connected to a source of laser radiation, and said distal ends having-output-devices, being positioned in said area of treatment; and
   wherein said distal end has a diffuser thereon to enable even distribution of said laser radiation in target tissue.

2. The laser delivery system according to claim 1, wherein said first means allows adjustment of said micro-needles' position within said spaced openings.

3. The laser delivery system according to claim 1, wherein said spaced openings are approximately 3 to 6 mm on center to adjacent openings.

4. The laser delivery system according to claim 3, wherein said spaced openings are uniformly positioned on said plate.

5. The laser delivery system according to claim 1, wherein each of said micro-needles is pointed at a distal tip to enhance penetration into said layer of skin.

6. The laser delivery system according to claim 1, wherein said third means is markings on said optical fibers for indicating distance into said micro-needles or tissue.

7. The laser delivery system according to claim 1, wherein said second means is bandages or straps.

8. The laser delivery system according to claim 1, wherein said first means is selected from the group consisting of weld, glue, and o-rings.

9. A photo dynamic therapy laser delivery system for the safe delivery of laser radiation to an area of treatment below a layer of skin comprising:
   a plate with a plurality of spaced openings, said plate having a treatment side and an insertion side, said spaced openings connecting said sides;
   micro-needles placed in the said spaced openings;
   first means for holding said micro-needles in said spaced openings in said plate; wherein said micro-needles extend beyond said treatment side, by a predetermined distance sufficient to penetrate through the skin;
   second means for holding said plate on said layer of skin;
   optical fibers placed in at least two of said micro-needles;
   third means for positioning said optical fibers in said micro-needles;
   wherein said optical fibers have proximal ends and distal ends, said proximal ends being connected to a source of laser radiation, and said distal ends having-output-devices, being positioned in said area of treatment; and
   wherein said third means is markings on said optical fibers for indicating distance into said micro-needles or tissue.

10. The laser delivery system according to claim 9, wherein said first means allows adjustment of said micro-needles' position within said spaced openings.

11. The laser delivery system according to claim 9, wherein said spaced openings are approximately 3 to 6 mm on center to adjacent openings.

12. The laser delivery system according to claim 11, wherein said spaced openings are uniformly positioned on said plate.

13. The laser delivery system according to claim 9, wherein each of said micro-needles is pointed at a distal tip to enhance penetration into said layer of skin.

14. The laser delivery system according to claim 9, wherein each said optical fiber with said distal end has a diffuser thereon to enable even distribution of said laser radiation in a target tissue.

15. The laser delivery system according to claim 9, wherein said second means is bandages or straps.

16. The laser delivery system according to claim 9, wherein said first means is selected from the group consisting of weld, glue, and o-rings.

* * * * *